(12) United States Patent
Enk (10) Patent No.: US 8,950,400 B2
(45) Date of Patent: Feb. 10, 2015

(54) GAS FLOW REVERSING ELEMENT

(75) Inventor: Dietmar Enk, Coesfeld (DE)

(73) Assignee: Dolphys Technologies B.V., Eindhoven (NL)

( * ) Notice: Subject to any disclaimer, the term of this patent is extended or adjusted under 35 U.S.C. 154(b) by 1208 days.

(21) Appl. No.: 12/561,208

(22) Filed: Sep. 16, 2009

(65) Prior Publication Data

US 2010/0236551 A1 Sep. 23, 2010

Related U.S. Application Data

(63) Continuation-in-part of application No. PCT/EP2008/053062, filed on Mar. 14, 2008.

(30) Foreign Application Priority Data

Mar. 16, 2007 (DE) .......................... 10 2007 013 385

(51) Int. Cl.
*A62B 9/00* (2006.01)
*F15C 1/08* (2006.01)
(Continued)

(52) U.S. Cl.
CPC ............ *A61M 16/00* (2013.01); *A61M 16/0833* (2014.02); *A61M 16/0012* (2014.02); *A61M 16/125* (2014.02); *A61M 16/0009* (2014.02); *A61M 16/0096* (2013.01);
(Continued)

(58) Field of Classification Search
CPC ..................... A61M 16/0009; A61M 16/0012; A61M 16/0096
USPC ............. 128/204.24, 204.25, 204.26, 205.12, 128/205.19, 205.27; 604/35
See application file for complete search history.

(56) References Cited

U.S. PATENT DOCUMENTS 3,581,742 A * 6/1971 Glenn ....................... 128/204.19
3,667,069 A * 6/1972 Blackshear et al. ........... 623/3.1
(Continued)

FOREIGN PATENT DOCUMENTS

| DE | 20213420 | 11/2002 |
|----|----------|---------|
| FR | 2287247 | 5/1976 |
| WO | WO 99/66975 | 12/1999 |

OTHER PUBLICATIONS

Comparison of four different emergency airway access equipment sets on a human patient simulator, Anaesthia, 2004, 59, pp. 73-79.
(Continued)

*Primary Examiner* — Lynne Anderson
*Assistant Examiner* — Bradley Philips
(74) *Attorney, Agent, or Firm* — Moore & Van Allen PLLC (57) ABSTRACT

A gas flow reversing element is provided comprising a main piece defining at least one closable outlet opening, a branching piece extending from the main piece, a line connector connected to the distal end of the branching piece, a pressure connector connected to the main piece, the pressure connector being structured to be fluidly connected to a pressurized gas supply; and a nozzle being configured and arranged in the main piece in such a way that a gas flow flowing in the main piece from the pressure connector through the nozzle to the at least one outlet opening, with the at least one outlet opening being disposed in the second open position, a gas flow can also be generated in the branching piece in a direction toward the at least one outlet opening.

34 Claims, 5 Drawing Sheets

(51) Int. Cl.
*A61M 16/00* (2006.01)
*A61M 16/08* (2006.01)
*A61M 16/12* (2006.01)
*A61M 16/14* (2006.01)

(52) U.S. Cl.
CPC ....... *A61M 16/14* (2013.01); *A61M 2202/0208* (2013.01); *A61M 2202/0468* (2013.01)
USPC ............. 128/204.25; 128/204.24; 128/205.19

(56) References Cited

U.S. PATENT DOCUMENTS

| | | | |
|---|---|---|---|
| 3,785,377 A * | 1/1974 | Jorgensen | 128/205.12 |
| 4,344,574 A * | 8/1982 | Meddings et al. | 239/338 |
| 4,519,388 A * | 5/1985 | Schwanbom et al. | 128/204.25 |
| 4,584,998 A | 4/1986 | McGrail | |
| 4,790,818 A * | 12/1988 | DeLuca et al. | 604/540 |
| 5,669,380 A | 9/1997 | Garry et al. | |
| 5,906,204 A * | 5/1999 | Beran et al. | 128/207.14 |
| 6,443,154 B1 * | 9/2002 | Jalde et al. | 128/205.29 |
| 7,174,894 B1 * | 2/2007 | Raspallo | 128/207.14 |
| 2004/0154617 A1 | 8/2004 | Enk | |

OTHER PUBLICATIONS

"A pressurized injection/suction system for ventilation in the presence of complete airway obstruction", Critical Care Medicine, vol. 22, No. 2, pp. 326-333.

International Search Report for PCT/EP2008/053062 dated Feb. 4, 2009.

International Preliminary Report on Patentability for PCT/EP2008/053062 dated Oct. 22, 2009.

Search Report for German Patent Application No. 10 2009 013 205.8 as issued Jun. 15, 2010.

* cited by examiner

GAS FLOW REVERSING ELEMENT

CROSS-REFERENCE TO RELATED APPLICATIONS

This is a continuation-in-part of International Application PCT/EP2008/053062, with an international filing date of Mar. 14, 2008, which in turn, claims priority to application number DE 10 2007 013 385.7, with a filing date of Mar. 16, 2007, both of which are hereby incorporated herein by reference.

FIELD OF THE INVENTION

The present invention relates to a gas flow reversing element and to a method for selectively generating a gas flow from or to a line connector for gas exchange in sealed or only partially ventilated rooms. One use involves connecting such a gas flow reversing element to a catheter or a cannula or needle (collectively the cannula or needle are referred to herein as a "cannula") insertable into the airways of a patient.

BACKGROUND OF THE INVENTION

To ventilate a patient, a mask or a tube is normally used by way of which a gas or gas mixture, in particular oxygen and air, is delivered at low pressure to the airway sealed off from the outside. Alternatively, however, a gas or gas mixture of this kind can also be injected in pulses at a high pressure and a high flow rate through a thin, unblocked catheter into the airway lying open to the outside (jet ventilation). This method is nowadays used particularly in diagnostic and therapeutic interventions in the area of the upper airway or of the lung. By means of this method, however, a patient can also be supplied with oxygen via a catheter introduced through the skin directly into the trachea or via a cannula positioned in this way (transtracheal jet ventilation). This special method is one of the currently available options for management of a difficult airway and, in particular, for management of the situation in which a patient cannot be conventionally ventilated or intubated (a "cannot ventilate, cannot intubate" situation).

Under unfavorable conditions, however, transtracheal jet ventilation can also be potentially life-threatening. If a patient's airway is substantially or even completely obstructed, for example by swelling or bleeding, the patient's lung becomes more and more distended by injection of oxygen. There is then a risk of barotrauma. The increase in pressure in the thorax can also lead to a circulatory disturbance, which is of no less danger to the patient, or to a circulatory collapse, since the blood is unable to flow back in sufficient quantity to the heart.

For some time, the "Oxygen Flow Modulator" has been known which, in the critical situation described, becomes the bidirectional airway. This is described, for example, on page 10 of a brochure "Products For the Difficult Airway" published in 2004 by Cook Medical Incorporated.

By intermittent closure and release of several openings, this instrument can be used not only to very easily control the flow of oxygen to the patient, but also to relieve the pressure in the thorax. Even in the case of a completely obstructed upper airway, this instrument is able to ensure the supply of oxygen to a patient, at least for a short time, by way of a catheter introduced into the trachea or by way of a cannula pushed into the trachea.

However, the ca. 3.5 liters of respiratory air which, in this situation with moderate volume expansibility of the thorax and normal airway resistances, are able to flow back out of the distended lung per minute and passively, i.e. only by means of the slight overpressure in the thorax, via a catheter with an internal diameter of 2.0 mm, are too little for adequate ventilation of an adult (hypoventilation). This results in carbon dioxide retention and, consequently, the rapid development of an undesired increase in the acid content of the blood (respiratory acidosis).

The "Oxygen Flow Modulator" in this connection achieves much more than conventional means with which it is possible merely to "inflate" the patient. However, it does not solve the problem that adult patients cannot be adequately ventilated through a catheter or a cannula of small cross section. This limitation, in addition to the risks mentioned, has in recent times led to a discussion in specialist journals concerning the role of emergency jet ventilation.

DE 20213420 U1 describes a ventilator, in particular for emergency transtracheal ventilation, with a controllable compressed gas source, a branched pipe for delivering and removing the respiratory gas to and from the patient, in which a venturi tube is intended to be used to assist the exhalation. This ventilator is constructed more like a suction device for lung secretions and the like, for which a high suction pressure is important, but not the greatest possible volumetric flow rates during suction. According to the specialist literature, this ventilator allows the respiratory minute volume to be increased by ca. 1 liter per minute through a catheter with an internal diameter of 2.0 mm. The resulting respiratory minute volume, however, is generally still not sufficient for normal ventilation of an adult. Moreover, the design does not provide any possibility of controlling with one hand the overpressure or underpressure acting in the direction of the patient.

Accordingly, the object of the present invention is to make available a simple device and a method by which oxygen can be delivered to the lung, but by which carbon dioxide or used air can also be actively withdrawn from the lung in sufficient quantity.

SUMMARY OF THE INVENTION

The foregoing object is achieved by a gas flow reversing element and associated method according to the embodiments of the invention described herein.

In one embodiment, the present invention provides a gas flow reversing element structured to be fluidly connected to a pressurized gas supply the gas flow reversing element comprising a main piece having first and second ends, the first end of the main piece defining at least one closable outlet opening, the at least one outlet opening being adjustable between a first closed state and a second open state. In one embodiment, at least one outlet opening is structured to switch between the first closed state and the second opened state. The gas flow reversing element comprises a branching piece extending from the main piece to a distal end and a line connector connected to the distal end of the branching piece. The gas flow reversing element comprises a pressure connector connected to the second end of the main piece, the pressure connector being structured to be fluidly connected to the pressurized gas supply. And the gas flow reversing element comprises a nozzle particularly an injector nozzle being configured and arranged in the main piece in such a way that a gas flow flowing in the main piece from the pressure connector through the nozzle to the at least one outlet opening, with the at least one outlet opening being disposed in the second open position, a gas flow can also be generated in the branching piece in a direction toward the at least one outlet opening, wherein the gas flow through the main piece from the branching piece to the at least one outlet opening has a flow cross section that is substantially constant or that increases in the direction of the at least one outlet opening. In one embodiment, the pressurized gas supply provides oxygen.

In one embodiment, at least one of the main piece, the branching piece and the fluid connection to the pressured gas supply defines at least one safety opening. In another embodiment, the incoming line from the pressurized gas supply may also define at least one safety hole. In another embodiment, at least one of the main piece and the branching piece defines two safety openings positioned adjacent to one another or positioned opposite one another. In another embodiment, the at least one outlet opening and the at least one safety opening are structured such that they can selectively be closed individually or together and completely or partially, for example manually, preferably with the ball of the thumb and/or with the fingers of just one hand of a helper.

In one embodiment, at least one of the branching piece and the line connected to the line connector defines a closable side access. In another embodiment, at least one of the pressure connector, the line connector, and the closable side access are structured as a Luer lock. In yet another embodiment, at least one of the main piece, the branching piece and the fluid connection to the pressured gas supply is structured so as to be closable to prevent the flow of gas therethrough. In still another embodiment, at least one of the main piece, the branching piece and the fluid connection to the pressured gas supply is structured so as to be automatically closable upon the occurrence of a predetermined condition to prevent the flow of gas therethrough.

In one embodiment, the gas flow reversing element comprises an ergonomically shaped housing adapted to the human hand.

In one embodiment, the main piece and the branching piece together form approximately a T-shaped configuration with the main piece as crossbeam. In another embodiment, the main piece and the branching piece together form approximately a Y-shaped configuration with the at least one outlet opening forming the bottom of the Y. In another embodiment, the gas flow reversing element comprises a housing and wherein the main piece and the branching piece are made substantially of plastic, and the nozzle comprises plastic or a metal insert, and the main piece including the pressure connector are encapsulated in the housing.

In one embodiment, the invention includes a gas flow reversing element structured to be fluidly connected to a pressurized gas supply, such as oxygen, the gas flow reversing element comprising a main piece having first and second ends, the first end of the main piece defining at least one closable outlet opening, the at least one outlet opening being adjustable between a first closed state and a second open state, and wherein the main piece defines a mixing channel. In one embodiment, the at least one outlet opening is structured to be rotated between the first closed state and the second opened state. The gas flow reversing element comprises a branching piece extending from the main piece to a distal end; a line connector connected to the distal end of the branching piece; a pressure connector connected to the second end of the main piece, the pressure connector being structured to be fluidly connected to the pressurized gas supply; and a nozzle, particularly an injector nozzle, being configured and arranged in the main piece in such a way that a gas flow flowing in the main piece from the pressure connector through the nozzle and through the mixing channel to the at least one outlet opening, with the at least one outlet opening being disposed in the second open position, a gas flow can also be generated in the branching piece in a direction toward the at least one outlet opening, wherein the gas flow through the main piece from the branching piece to the at least one outlet opening has a flow cross section that is substantially constant or that increases in the direction of the at least one outlet opening with a volumetric flow rate which, at an excess pressure of 0.5 to 5 bar above atmospheric pressure at the pressure connector, is at least 8 liters per minute.

In one embodiment, the volumetric flow rate in the branching piece is at least 0.4 times the volumetric flow rate through the pressure connector, in both the (partially) closed and the open position, at an excess pressure of 0.5 to 5 bar at the pressure connector. In another embodiment, the volumetric flow rate in the branching piece is approximately 0.4 to 2 times the volumetric flow rate through the pressure connector, in both the (partially) closed and the open position, at an excess pressure of 0.5 to 5 bar at the pressure connector.

In one embodiment, the length of the mixing channel and the internal diameter of the nozzle have a ratio of between 2:1 and 200:1. In another embodiment, the length of the mixing channel and the internal diameter of the nozzle have a ratio of between 5:1 and 100:1. In yet another embodiment, the internal diameter of the mixing channel and the internal diameter of the nozzle have a ratio of between 2:1 and 6:1. In still another embodiment, the ratio of the internal diameter of the mixing channel and the internal diameter of the branching piece is between 1:2 and 2:15. In one embodiment, the ratio of the internal diameter of said mixing channel and said internal diameter of said branching piece is between 1:2 and 2:1. In one embodiment, the ratio of the internal diameter of the mixing channel and the internal diameter of the branching piece is 2:2.5.

In one embodiment, at least one of the main piece and the branching piece defines at least one safety opening. In another embodiment, the at least one safety opening are structured such that they can selectively be closed individually or together and completely or partially, for example manually, preferably with the ball of the thumb and/or with the fingers of just one hand of a helper. In another embodiment, at least one of the main piece and the branching piece defines two safety openings positioned adjacent to one another or positioned opposite one another.

In one embodiment, the branching piece and the line connected to the line connector defines a closable side access. In another embodiment, at least one of the pressure connector, the line connector, and the closable side access are structured as a Luer lock.

In one embodiment, the gas flow reversing element comprises an ergonomically shaped housing adapted to the human hand. In another embodiment, the main piece and the branching piece together form approximately a T-shaped configuration with the main piece as crossbeam. In another embodiment, the main piece and the branching piece together form approximately a Y-shaped configuration with the at least one outlet opening forming the bottom of the Y.

In one embodiment, the present invention provides a method for operating a gas flow reversing element, comprising providing a gas flow reversing element comprising a main piece having first and second ends, the first end of the main piece defining at least one closable outlet opening, the at least one outlet opening being adjustable between a first closed state and a second open state; a branching piece extending from the main piece to a distal end; a line connector connected to the distal end of the branching piece; a pressure connector connected to the second end of the main piece, the pressure connector being structured to be fluidly connected to the pressurized gas supply; and a nozzle, particularly an injector nozzle, being configured and arranged in the main piece in such a way that a gas flow flowing in the main piece from the pressure connector through the nozzle to the at least one outlet opening, with the at least one outlet opening being disposed in the second open position, a gas flow can also be generated in the branching piece in a direction toward the at least one outlet opening, wherein the gas flow through the main piece from the branching piece to the at least one outlet opening has a flow cross section that is substantially constant or that increases in the direction of the at least one outlet opening. The method includes providing a catheter or a cannula; connecting the catheter or the cannula to the line connector with or without a tube in between; inserting the catheter or cannula into the airway of a patient; supplying gas from a pressurized gas supply to the pressure connector of the gas flow reversing element wherein a substantially constant gas pressure is applied to the pressure connector, and, in order to generate a gas flow to the line connector, the at least one outlet opening is closed and, in order to generate a gas flow from the line connector in the direction of the at least one outlet opening, the at least one outlet opening is opened. In one embodiment, the branching piece of the gas flow reversing element defines a closable side access and the method further comprises providing a measuring device for measuring carbon dioxide content; and attaching the measuring device to the closable side access so that the measuring device can measure the carbon dioxide content of the gas or gas mixture flowing past the closable side access.

In one embodiment, the invention provides a method for ventilating a patient, or assisting the breathing of a patient, comprising providing a gas flow reversing element comprising a main piece having first and second ends, the first end of the main piece defining at least one closable outlet opening, the at least one outlet opening being adjustable between a first closed state and a second open state; a branching piece extending from the main piece to a distal end; a line connector connected to the distal end of the branching piece; a pressure connector connected to the second end of the main piece, the pressure connector being structured to be fluidly connected to the pressurized gas supply; and a nozzle, particularly an injector nozzle, being configured and arranged in the main piece in such a way that a gas flow flowing in the main piece from the pressure connector through the nozzle to the at least one outlet opening, with the at least one outlet opening being disposed in the second open position, a gas flow can also be generated in the branching piece in a direction toward the at least one outlet opening, wherein the gas flow through the main piece from the branching piece to the at least one outlet opening has a flow cross section that is substantially constant or that increases in the direction of the at least one outlet opening. The method includes providing a catheter or a cannula; connecting the catheter or the cannula to the line connector with or without a tube in between; inserting the catheter or cannula into the airway of a patient; and supplying oxygen from a pressurized gas supply to the pressure connector of the gas flow reversing element wherein an excess pressure of between 0.5 and 5 bar is set up at the pressure connector and the at least one outlet opening is closed intermittently such that oxygen passes into the patient's airway and the at least one outlet opening is opened at intervals in order to aspirate gas out from the patient's airway. In one embodiment, the branching piece of the gas flow reversing element defines a closable side access and the method further comprising providing a measuring device for measuring carbon dioxide content; attaching the measuring device to the closable side access so that the measuring device can measure the carbon dioxide content of the gas or gas mixture flowing past the closable side access; and opening the at least one outlet opening at intervals and for at least long enough to generally maintain a characteristic measured value of carbon dioxide content for the gas or gas mixture aspirated from the airway.

In one embodiment, the invention provides a method of ameliorating breathing obstructions in a subject, comprising providing a gas flow reversing element comprising a main piece having first and second ends, the first end of the main piece defining at least one closable outlet opening, the at least one outlet opening being adjustable between a first closed state and a second open state; a branching piece extending from the main piece to a distal end; a line connector connected to the distal end of the branching piece; a pressure connector connected to the second end of the main piece, the pressure connector being structured to be fluidly connected to the pressurized gas supply; and a nozzle, particularly an injector nozzle, being configured and arranged in the main piece in such a way that a gas flow flowing in the main piece from the pressure connector through the nozzle to the at least one outlet opening, with the at least one outlet opening being disposed in the second open position, a gas flow can also be generated in the branching piece in a direction toward the at least one outlet opening, wherein the gas flow through the main piece from the branching piece to the at least one outlet opening has a flow cross section that is substantially constant or that increases in the direction of the at least one outlet opening. The method includes providing a catheter or a cannula; connecting the catheter or the cannula to the line connector with or without a tube in between; inserting the catheter or cannula into the airway of a patient; supplying oxygen from a pressurized gas supply to the pressure connector of the gas flow reversing element; and opening and closing the at least one outlet opening intermittently to inspirate and aspirate the subject such that the subject is normoventilated. In one embodiment, the catheter has a maximum diameter of 3.5 mm. In another embodiment, the flow rate of the inspirated and aspirated gas is approximately 12 to 20 liters per minute. In yet another embodiment, the flow rate of the inspirated and aspirated gas is approximately 15 liters per minute.

BRIEF DESCRIPTION OF THE SEVERAL VIEWS OF THE DRAWINGS

Further details and advantages of the invention and preferred illustrative embodiments are explained in more detail below with reference to the drawings, in which.

DETAILED DESCRIPTION OF THE INVENTION

The detailed description begins with a general description of the invention and then concludes with the illustrative embodiments of the invention illustrated in FIGS. 1-6, which do not however limit the invention.

The gas flow reversing element according to the invention serves for the use of a gas supply under excess pressure, in particular oxygen, for selectively generating a gas flow from or to a line connector, in particular for connection to a catheter or cannula that can be inserted into the airway of a patient. It is designed as a main piece with a branching piece, which main piece connects a pressure connector, for connection to the gas supply, to at least one closable outlet opening, and which branching piece leads from the main piece to a line connector. A nozzle, particularly an injector nozzle, is configured and arranged in the main piece in such a way that, by a gas flow flowing from the pressure connector through the nozzle to the outlet opening, a gas flow can also be generated in the branching piece in the direction of the outlet opening, and, from the branching piece as far as the outlet opening, the main piece has a flow cross section that is substantially constant or that increases in the direction of the outlet opening. For the nozzle, it is in fact possible to choose any design principle that generates a suction effect by means of a gas flow.

However, the principle of a gas jet pump is preferably used here. Particularly with a view to aspirating large volumes of gas, it is important to manage as far as possible without any reduction in cross section in the main piece between the branching piece and the outlet opening.

There are various possible ways of achieving a good function of the gas flow reversing element. It has been found in tests that there are nozzle and mixing channel dimensions that show good results at subsonic speed, but it is also possible to use dimensions for a nozzle outlet speed in the supersonic range.

Experiments have shown that in one embodiment of the invention the spread of the gas stream after emergence from the nozzle into a mixing channel can be divided into three characteristic areas, namely the widening area, the eddy area, and the area of uniform movement. The widening area begins directly at the outlet of the nozzle. At this location, the stream of air is unable to follow the sharp edge of the nozzle and widens along a length corresponding to ca. 3 to 5 times the diameter of the nozzle. The widening area is followed by the eddy area, where a turbulent flow forms in the gas stream. In this area, the inflowing gas is mixed with the gas located in the main piece and is transported together with this in the direction of the outlet opening. The eddy area generally forms along a length that corresponds to ca. 5 to 7 times the diameter of the nozzle. The eddy area is followed by the area of uniform movement where the inflowing gas is mixed homogeneously with the gas previously located in the main piece. Here, there are virtually no turbulent flows any longer, and instead the gas or gas mixture moves uniformly in the direction of the outlet opening. Thus, the mixing channel should at least have a length corresponding to 8 times the nozzle diameter. Lengths of the mixing channel are preferred that correspond to 5 to 30 times the diameter of the nozzle.

In diameter, the lumen of the branching piece and the lumen of the main piece between nozzle and outlet opening are preferably not smaller than the lumen of the catheter or cannula insertable into the airway of a patient (e.g. at least 2 mm when using a catheter with an internal diameter of 2 mm), since otherwise an additional resistance is created that disturbs in particular the outward flow or aspiration of gas from the lung. A much larger opening or openings to the branching piece again lead to the design problem of accommodating these in or on the smaller lumen of the main piece. This, like a much larger lumen of the branching piece too, is also without any relevant effect on the flow resistance, which is then determined mainly by the catheter or cannula insertable into the airway of a patient.

The described design not only allows a gas or gas mixture under excess pressure to be delivered to a catheter or cannula and thus generate a gas flow there in the direction of the patient, it also permits use of a gas flow or gas mixture flow to generate an underpressure and thus generate a gas flow in a catheter or cannula away from the patient. This can be done selectively by opening and closing the outlet opening, even though the gas flow reversing element is supplied only with excess pressure.

For patient safety, it is important that no effect is made on the airway in the event of unintentional manipulation of the gas flow reversing element. It is therefore advantageous if at least one safety opening is present, preferably in the branching piece. There should preferably be two safety openings, particularly preferably two safety openings lying next to each other or opposite each other. These safety openings serve at the same time to control the overpressure or underpressure in the direction of the patient. When released, they additionally act as pressure compensation openings and permit compensation of an intrathoracic overpressure or underpressure when the jet ventilation is briefly stopped. In this way, the pressure in the lung can be balanced with the outside pressure. This is particularly important when there is a completely obstructed airway and it is not known whether the patient's lung is in fact inflated slightly too much or has been emptied.

When the pressure connector of the gas flow reversing element is connected to a compressed gas source, gas flows through the nozzle to the outlet opening, which, without safety openings, leads directly to an underpressure at the line connector and thus possibly also in the airway. This is avoided by the still open safety openings, which for this purpose should have a sufficiently large cross section, since the underpressure is compensated by ambient air flowing in there. It is only when all the safety openings have been deliberately closed, e.g. by an operator's fingers, that an underpressure arises at the line connector.

By additional closure of the outlet opening, a gas or gas mixture can then also be conveyed into the airway. By contrast, when the safety openings are released, the gas or gas mixture escapes immediately into the ambient air. Effective ventilation is achieved by selectively opening and closing the outlet opening while the safety openings are closed. The outlet opening is preferably shaped as an outwardly opening funnel that cannot unintentionally be closed so easily as a small outlet opening.

Particularly in emergency care, it is advantageous, according to a preferred embodiment of the invention, to arrange the outlet opening and the safety openings in such a way that they can selectively be closed individually or together, completely or partially, for example manually, preferably with the ball of the thumb and/or with the fingers of just one hand of a helper or of an operator. Thus, with one hand, a helper can perform the ventilation as required, interrupt the ventilation or regulate it by partially closing the openings, while still having the other hand free for other measures or activities (e.g. securing the catheter or cannula).

The pressure connector of the gas flow reversing element is preferably designed to establish a connection to a compressed gas source, preferably a compressed oxygen cylinder. Most vehicles for emergency medical treatment and most casualty wards have at least one small compressed oxygen cylinder (e.g. 2 liters) with which the gas flow reversing element can be operated for a period of at least 20 minutes.

It may be necessary to admix medicaments to the gas or gas mixture. For this purpose, a closable side access can be arranged particularly advantageously on the branching piece, preferably between the safety openings and the line connector. Thus, for example, adrenaline, local anesthetics, expectorants and the like can be conveyed in finely atomized form to the patient by means of the rapidly flowing gas or gas mixture. In this way, a medicament can be distributed effectively and over a large surface area into the bronchi and is thus more rapidly absorbed. The side access also provides a possible connection for a capnometry line via which a small sample for measuring the carbon dioxide concentration can be removed from the aspirated respiratory air in the secondary stream. This permits ongoing determination of the efficiency of the ventilation (ventilation decreasing or increasing over time). Direct or indirect attachment of a gas flow meter or pressure meter is also conceivable.

According to the invention, the main piece and the branching piece preferably together form what is approximately a T-piece, with the main piece as the crossbeam. This makes the structure particularly noticeable and the nozzle construction very simple.

Alternatively, according to the invention, a gas flow reversing element is proposed in which the main piece and the branching piece together form what is approximately a Y-piece, with the outlet opening forming the foot of the Y. An arrangement in which the branching piece is at an angle of between 10° and 90° with respect to a straight main piece may also be advantageous in terms of the flow.

To simplify production, the gas flow reversing element according to the invention is preferably assembled, in particular screwed together, from several component parts. This permits the use of standard components for part of the arrangement.

It is also preferable for the pressure connector and/or the line connector, and if appropriate the side access, to be designed as a Luer lock, in order to permit pressure-tight connection to standard components.

For safety reasons, it appears expedient to encapsulate the high-pressure part of the gas flow reversing element, including the connecting tube attachment.

Generally, the gas flow reversing element according to the invention should be made substantially of plastic, the nozzle being composed of plastic or of a metal insert.

The method according to the invention for operating a gas flow reversing element will be explained in detail below. The method is basically one in which a substantially constant gas pressure, in particular oxygen pressure, is applied to the pressure connector, and, in order to generate an overpressure at the line connector, the outlet opening and if appropriate all the safety openings are closed and, in order to generate an underpressure, the outlet opening is opened, if appropriate with the safety openings still closed.

By means of this principle of aspirating respiratory air via a catheter or cannula insertable into the airway of a patient, the gas flow reversing element can be combined in a very practicable way with conventional jet ventilation. It is in this way possible, not only in emergency cases, for a patient to be efficiently ventilated (i.e. sufficiently supplied with oxygen while at the same time carbon dioxide is removed) via conduits of small cross section (e.g. catheters or cannulas inserted transcutaneously into the trachea, but also so-called tube changers or working channels of flexible fiber optics). It is unimportant whether the upper airway is open, as is essential in conventional jet ventilation, or is by contrast partially or even completely obstructed.

For the use of the gas flow reversing element according to the invention, only a compressed oxygen cylinder and a connecting line are needed. The gas flow reversing element can be designed such that it can be adapted or constructed in particular also for different pressures of the oxygen sources. For example, oxygen sources have an outlet pressure of 3.5 bar in the United States and, by contrast, of up to 5 bar in Europe.

An important variable in the gas flow reversing element is the emission pressure at the nozzle, by which an underpressure is generated at the line connector. The emission pressure correlates directly with the flow and the resulting speed of flow of the gas or gas mixture through the gas flow reversing element, and the speed of flow of the gas or gas mixture in turn correlates with the underpressure at the line connector. With a view to the considerable suction performance that is desired, it is necessary to work with very high gas speeds. These can be achieved preferably by injector nozzle openings of 1 mm or less. A compressed gas flow of 15 liters per minute through such a nozzle can give gas speeds in the supersonic range. It is also important that the generated underpressure in the branching piece can be converted into a relatively high gas flow, which is best achieved if there are no reductions in cross section significantly impeding the gas flow in the main piece between the branching piece and the outlet opening.

The gas flow reversing element can also be combined with an upstream flow meter. This permits very simple and quick adaptation to the patient (e.g. children are in this way ventilated with a lower oxygen flow and thus with a lower emission pressure at the nozzle and thus also a lower underpressure at the line connector). A reduction in the gas (mixture) flow always results in weaker ventilation (reduction of the respiratory minute volume), while an increase in the gas (mixture) flow always results, by contrast, in stronger ventilation (increase of the respiratory minute volume).

Since a typically used catheter or cannula provides a considerable flow resistance, the overpressure or the underpressure acting alternately at the line connector is attenuated. Pressure changes in the lung of a patient are always attenuated primarily by the gas volume still present in the lung after normal exhalation (functional residual capacity) and secondarily by the elastic thoracic wall and the displaceable diaphragm. The danger of barotrauma is minimized in this way. Barotrauma is basically only possible upon prolonged incorrect operation of the gas flow reversing element by the user. Thus, the risk of collapsing lung sections (development of atelectasis) in the event of an excessively long and strong aspiration of respiratory air from the lung is countered by what is in emergency situations a desired positive circulatory effect, while a low pressure in the thorax improves the return flow of blood to the heart.

In ventilation tests in a lung model using an oxygen flow of 15 liters per minute and an overpressure of ca. 1 bar above atmospheric pressure, and using a transtracheal catheter measuring approximately 10 cm in length and with an internal diameter of 2 mm, a respiratory minute volume of more than 6 liters per minute was measured, which is sufficient for ventilating an adult. This gives a ratio of at least 0.4:1, preferably 0.6:1 to 2:1, between the volumetric flow rate through the branching piece and the volumetric flow rate through the pressure connector. It should also be noted here that, in jet ventilation through a transtracheal catheter, there is no anatomical dead space and, therefore, a smaller respiratory minute volume is in principle already enough for sufficient ventilation (called normal ventilation) of a patient.

A noticeable aspect of the tests was a more or less physiological relation between inhalation time and exhalation time (here the time of injection of oxygen, and the time of aspiration of respiratory air). This minimizes ventilation-induced circulatory problems. By contrast, passive removal of respiratory air through such a transtracheal catheter results in a grotesque inhalation/exhalation ratio, with an exhalation time longer by a multiple than the inhalation time.

Limiting the underpressure in relation to atmospheric pressure (relative pressure) to approximately −0.3 bar, which was achieved in tests, is advantageous. If the catheter or cannula lies on the mucosa, it cannot aspirate too strongly and cause local damage to the mucosa. The principle used causes the catheter or cannula to be forced away from the mucosa upon each injection.

The simple "switching" between overpressure and underpressure functions well and is virtually without risk to the patient and user, with cyclical reversal of flow and pressure in the gas flow reversing element, and opens up new possibilities particularly in emergency ventilation. The absence of any mechanisms or movable parts not only makes the relatively small device maintenance-free, but also makes it easy to understand and safe to use. Something potentially dangerous (under very unfavorable conditions) can happen only as a result of deliberate manipulation by the user, not by connection of the gas flow reversing element as such or by the loosening of a connected compressed gas source.

The range of use, however, goes far beyond the "cannot ventilate, cannot intubate" situation. A patient with only a partially or temporarily obstructed upper airway will no doubt also benefit from this ventilation principle, the suction-assisted exhalation providing a virtually greater free airway. Even in patients with an open upper airway, it is to be expected that more efficient gas exchange and greater gas conversion in the lung will result in more rapid oxygen enrichment and at the same time more effective carbon dioxide elimination.

There is also the possibility of simple jet ventilation. For this, the outlet opening and the safety openings simply have to be closed simultaneously and then released again, i.e. suction-assisted exhalation is only an option that can be used; it does not have to be used.

The implementation of this principle in conventional jet ventilators is desirable. Today's devices all require a sufficiently large, free upper airway in the patient. In the event of substantial or complete obstruction of the airway (e.g. by instrumentation), these devices stop as soon as too high a pressure is measured in the airway, with the result that the patient is no longer ventilated. Based on the present invention, jet ventilators can be constructed which, independently of the free cross section of the airway and even in cases of complete obstruction of the airway, are able to ventilate a patient not only sufficiently, but also very safely and effectively.

Starting out from the operating principle of the gas flow reversing element, very precise control of the inhalation/exhalation ratio and of the ventilation frequency could be achieved by means of an apertured disk or apertured wheel that rotates about the outlet opening. By suitable cutouts in this apertured disk or apertured wheel, inhalation time and exhalation time could therefore be determined in such a way that the injected gas (mixture) volume is subsequently removed again. With a rapidly rotating apertured disk or apertured wheel, it would also be relatively simple to achieve ventilation frequencies in the sense of high-frequency ventilation (e.g. for lung-protective ventilation of critically ill patients) which, in conventional devices, require considerably greater outlay in technical terms. This would open up entirely new possibilities in diagnostic and therapeutic interventions.

Figure 1:
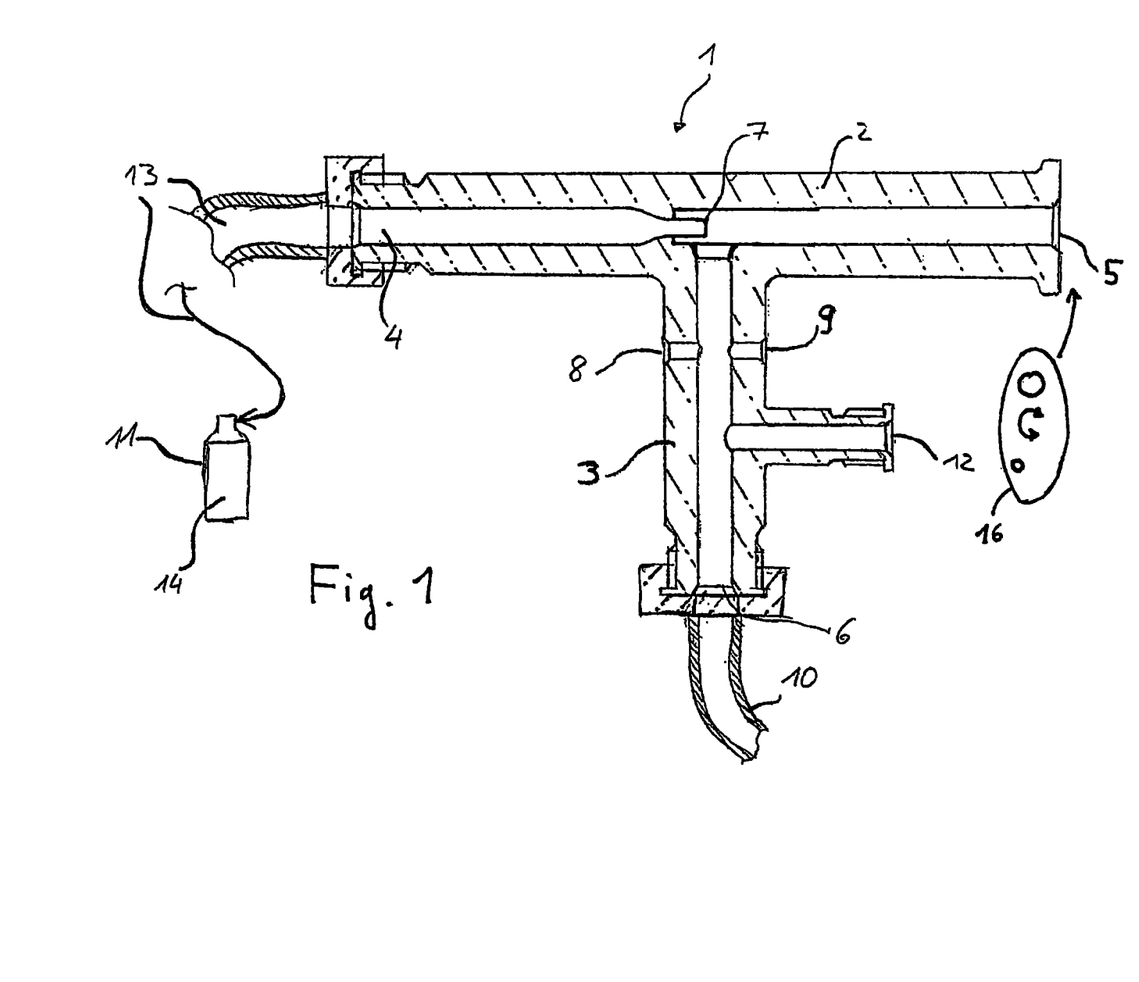
FIG. 1 shows a longitudinal section through a gas flow reversing element according to the invention, with peripheral devices indicated schematically.

In FIG. 1, a gas flow reversing element 1 is shown with a main piece 2 which connects a pressure connector 4 to an outlet opening 5. The pressure connector 4 can be connected by a connecting line 13 to a gas supply 14 which is under excess pressure in a compressed gas source 11. A compressed oxygen cylinder is generally made available for the emergency care of patients. Extending off from the main piece 2 is a branching piece 3, which leads to a line connector 6. In the main piece 2 there is a nozzle 7 through which gas can flow from the pressure connector 4 to the outlet opening 5. This nozzle 7 lies near the branching piece 3, such that the gas flowing through the nozzle to the outlet opening 5 generates an underpressure in the branching piece 3. Here, the principle of a gas jet pump is used. However, it is possible to choose any arrangement that is able to generate a suction effect by means of a gas flow. For this purpose, it is in particular not necessary for the branching piece 3, as shown in the illustrative embodiment, to form a right angle α (alpha) with the main piece 2. Moreover, the branching piece 3 has a first safety opening 8 and a second safety opening 9. As long as these two safety openings 8, 9 are not deliberately closed, the device, even with gas flowing through it, does not exert any influence on the airway of a patient. It is only when these safety openings 8, 9 are closed that an underpressure is generated in the branching piece 3, as long as the outlet opening 5 is open, and an overpressure when the outlet opening 5 is closed. All the openings should preferably be arranged in such a way that, although an operator can intentionally close them using one hand, they cannot be closed unintentionally. At least the outlet opening 5 should be able to be closed with one finger, since it has to be selectively opened and closed during ventilation. Here too, in order to avoid unintentional actuation as far as possible, the main piece 2 can be widened in a funnel shape before the outlet opening 5. As is indicated schematically, a rotatable apertured disk 16 with holes of different sizes can also be arranged before the outlet opening 5 and can then be turned to the respectively desired position by an operator. The branching piece 3 also has a closable side access 12 through which medicaments can be added or probes inserted. A catheter 10 or a cannula can be attached to the line connector 6. Each of the connectors is preferably designed as a Luer lock. The whole arrangement is preferably made of plastic, although, if so required, the nozzle 7 can also be fitted as a metal part.

Figure 2:
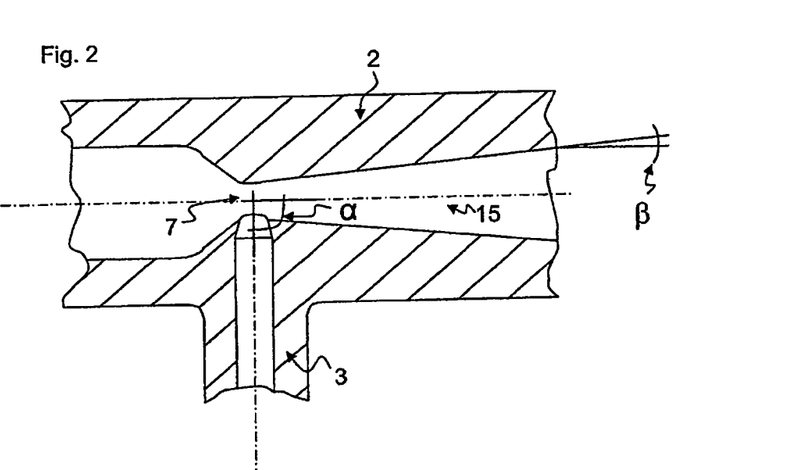
FIG. 2, FIG. 3 and FIG. 6 show alternative embodiments of nozzle and main piece.
Figure 3:
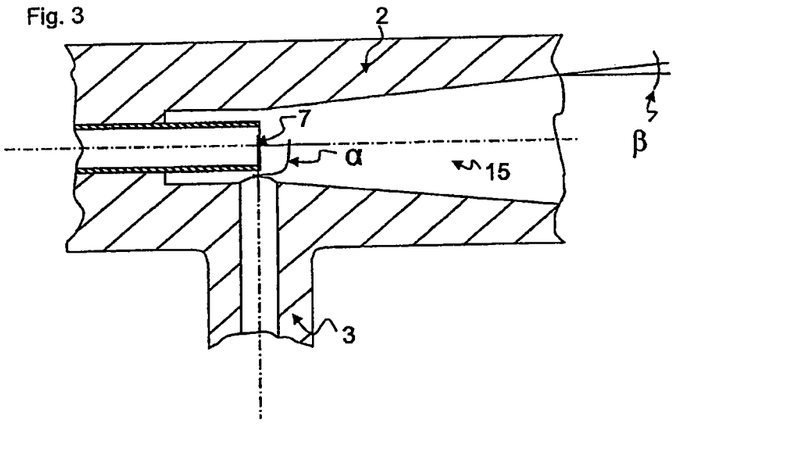
Figure 6:
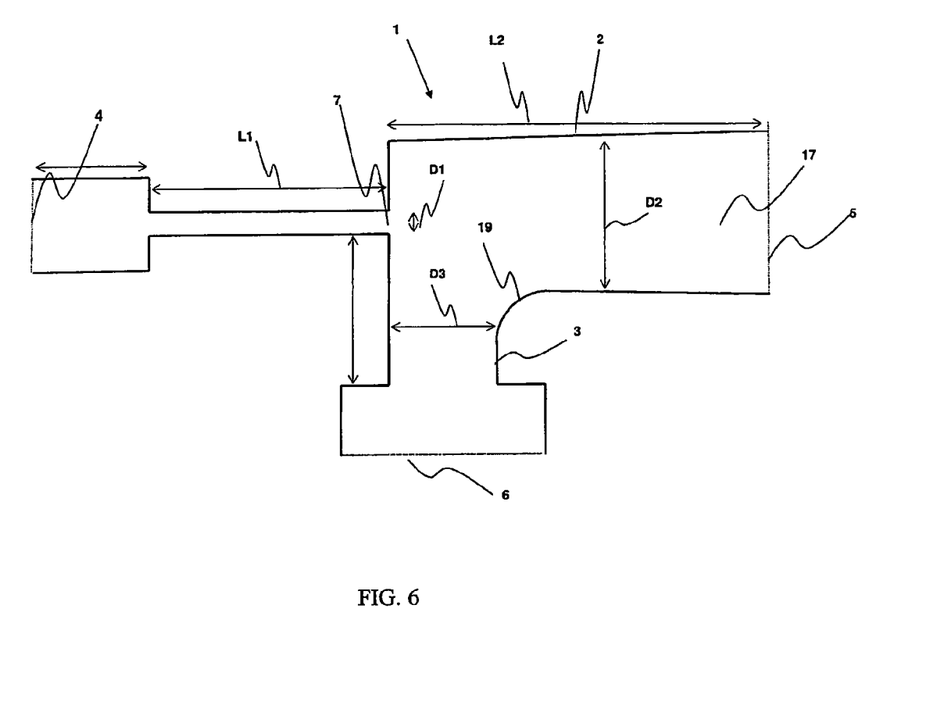

FIGS. 2, 3 and 6 show alternative embodiments of the main piece 2 and of the nozzle 7. FIG. 2 shows an embodiment of the main piece 2 as a venturi tube in which the branching piece 3 opens in at the point of greatest speed and therefore of lowest pressure. In both of FIGS. 2 and 3, the main piece 2, at the area behind the branching piece 3, forms a channel 15 that widens conically with an opening angle β (beta) of 1° to 7°, for example.

Figure 4:
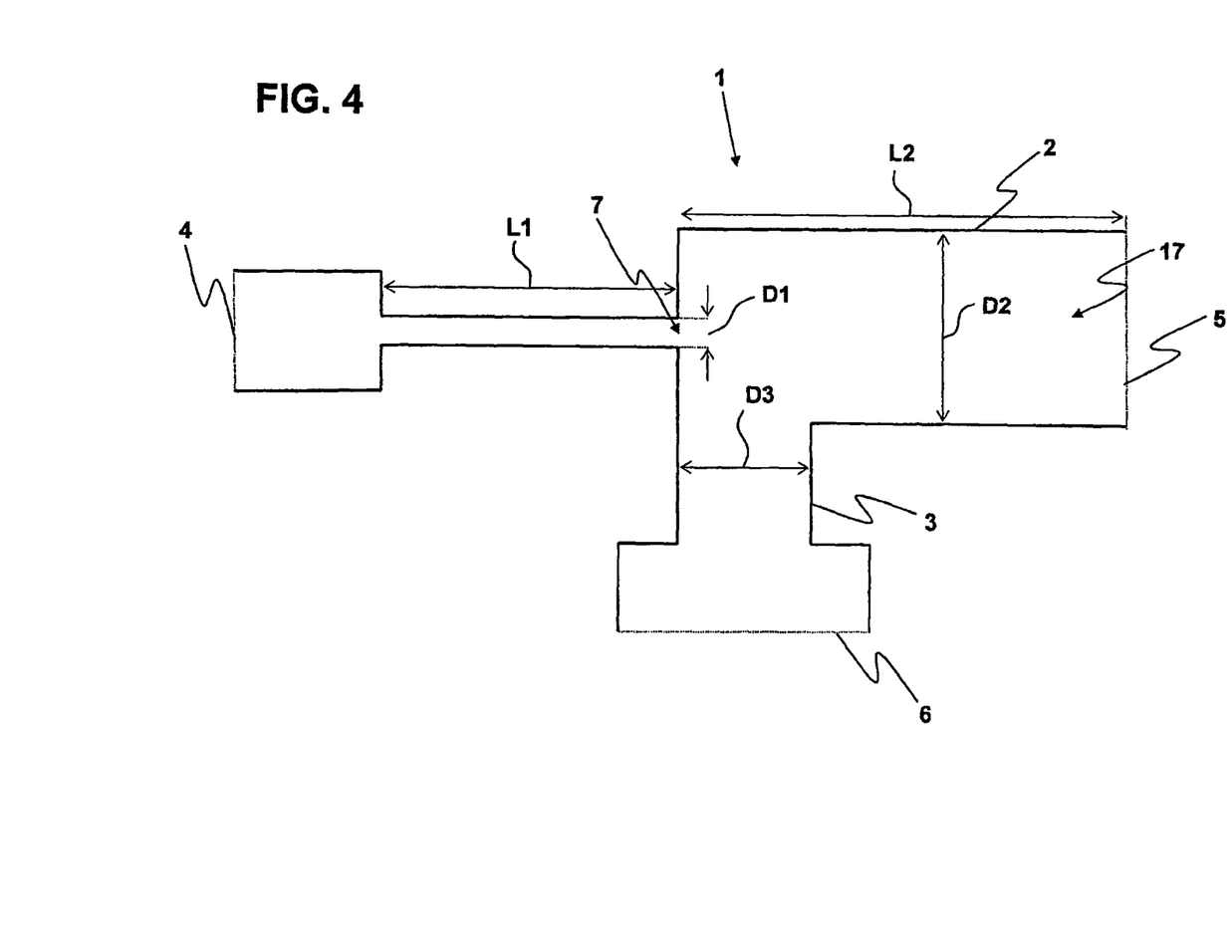
FIG. 4 is a diagram showing the size ratios of individual parts of the gas flow reversing element.

FIG. 4 shows another schematic representation of an embodiment of the gas flow reversing element 1 with main piece 2 and branching piece 3. Here, D1 designates the internal diameter of the nozzle 7, D2 the internal diameter of the mixing channel 17, and D3 the internal diameter of the branching piece 3. L1 designates the length of the nozzle 7, and L2 the length of the mixing channel 17. In a preferred functional test arrangement, the internal diameter D1 of the nozzle 7 was between 0.5 and 2 mm, preferably 1 mm, and the internal diameter D2 of the mixing channel 17 was between 1 and 5 mm, preferably 2 to 3 mm, in particular 2.5 mm. The internal diameter D3 of the branching piece 3 was of the same order of magnitude as the internal diameter D2 of the mixing channel 17. The length L1 of the nozzle 7 was 5 to 20 mm, preferably 15 mm. The length L2 of the mixing channel was 10 to 40 mm, preferably 20 to 30 mm, and the ratio of the length L2 of the mixing channel 17 and the internal diameter D1 of the nozzle 7 was between 2:1 and 100:1, preferably between 5:1 and 50:1.

Figure 5:
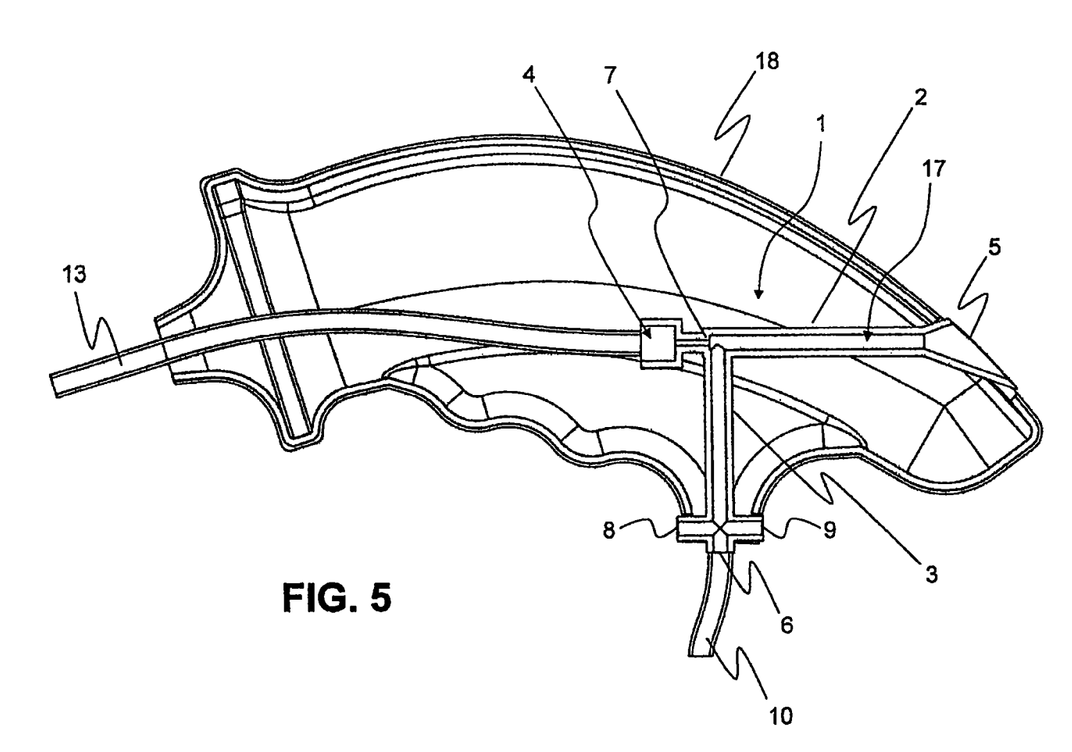
FIG. 5 shows a gas flow reversing element with an ergonomically shaped housing.

FIG. 5 shows another embodiment of the gas flow reversing element 1, in which the gas flow reversing element 1 is arranged in an ergonomically shaped housing 18. The housing 18 is shaped in such a way that it is adapted to the human hand. The safety openings 8, 9 can be completely or partially closed with the fingers, and the outlet opening 5 with the thumb. It does not matter whether the outlet opening 5, the safety openings 8, 9, the pressure connector 4 and/or the line connector 6 are mounted directly on the outer wall of the housing or whether the respective connection between the opening or connector and the outer wall of the housing is embodied by a line section, for example a connecting line 13. By means of such a configuration, a helper can operate the gas flow reversing element 1 using just one hand. For easier handling, it is also possible to provide just one safety opening 8. The housing 18 and the gas flow reversing element 1 can be assembled in different ways or produced in one piece. The important thing is that a device is obtained which is easy to operate manually and can be held in one hand, with the outlet opening 5 and the safety openings 8, 9 being able to be closed off by the fingers or by other parts of this hand.

The present invention permits effective ventilation of a patient. Under emergency conditions, in addition to a catheter 10 or cannula that can be inserted into a patient's airways, and a connecting line 13, all that is needed is a compressed gas source 11, e.g. a compressed oxygen cylinder. This ventilating technique provides a high degree of safety for patient and helper. It can also be used as a means of respiratory assistance to support the respiration of a patient who is breathing spontaneously.

The gas flow reversing element and the method for operating the gas flow reversing element according to the present invention can in particular be used for ventilation of a patient, in particular a patient having no adequate respiratory function on his own, with expiratory assistance by suction.

The method for ventilation of a patient with expiratory assistance by suction can in particular be used in case of one of the following indications:

a) transtracheal jet ventilation;

b) ventilation via conduits of small cross section (e.g., catheters) in case of obstructed, nearly complete or even completely blocked airways due to pharyngeal, laryngeal, tracheal or bronchial tumor (e.g., carcinoma, submucosal edema, bleeding, emphysema);

c) one lung ventilation via conduits of small cross section; and d) diagnostic and/or therapeutic intervention in the airway limiting the size of the artificial airway (e.g., endotracheal tube) that can be placed for maintaining adequate ventilation.

The method for ventilation of a patient with expiratory assistance by suction can in particular be used in case of one of the following medical conditions:

a) pharyngeal, laryngeal, tracheal, bronchial airway obstruction limiting passive backflow from the lungs;

b) pharyngeal, laryngeal, tracheal, bronchial airway obstruction limiting the size of an artificial airway (e.g., endotracheal tube) that can be placed for maintaining adequate ventilation;

c) pharyngeal, laryngeal, tracheal, bronchial airway obstruction limiting the size of the artificial airway (e.g., endotracheal tube) that can be placed for maintaining adequate ventilation during diagnostic and/or therapeutic interventions in the airway;

d) "cannot ventilate, cannot intubate" situation; and e) support of cardiocirculatory resuscitation by alternately creating negative and positive intrathoracic pressure.

Furthermore, for the gas flow reversing element, according to the present invention, the outlet opening of the nozzle is preferably positioned in front or above the branching piece. This improves the efficiency of the jet entrainment effect in the element according to the present invention.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

The invention claimed is:

1. A gas flow reversing apparatus, the gas flow reversing apparatus comprising:

a ventilating pressurized gas supply, the ventilating pressurized gas supply supplying oxygen; and a gas flow reversing element comprising:

a main piece having first and second ends, said first end of said main piece defining at least one closable outlet opening, said at least one outlet opening being adjustable between a first closed state and a second open state;

a branching piece extending from said main piece to a distal end;

a line connector connected to said distal end of said branching piece;

a pressure connector connected to said second end of said main piece, said pressure connector being fluidly connected to the ventilating pressurized gas supply; and a nozzle being configured and arranged in said main piece in such a way that, when said at least one outlet opening is disposed in said second open state, a gas flow generated by the ventilating pressurized gas supply (i) flows to said pressure connector and through said nozzle to said at least one outlet opening and (ii) generates a gas flow in said branching piece in a direction toward said at least one outlet opening, wherein the gas flow through said main piece from said branching piece to said at least one outlet opening has a flow cross section that is substantially constant or that increases in the direction of said at least one outlet opening, said nozzle also being configured and arranged in said main piece in such a way that, when said at least one outlet opening is disposed in said first closed state, a gas flow generated by the ventilating pressurized gas supply flows to said pressure connector and through said distal end of said branching piece towards said line connector; and wherein the gas flow reversing element is arranged in an ergonomically shaped housing and the at least one closable outlet opening of the main piece is configured to be closed by closing an opening in the ergonomically shaped housing.

2. The gas flow reversing apparatus according to claim 1 wherein at least one of said main piece, said branching piece and said fluid connection to said pressured gas supply defines at least one safety opening.

3. The gas flow reversing apparatus according to claim 2 wherein said at least one outlet opening and said at least one safety opening are structured such that they can selectively be closed either individually or together and either completely or partially.

4. The gas flow reversing apparatus according to claim 2 wherein at least one of said branching piece and the line connected to said line connector defines a closable side access.

5. The gas flow reversing apparatus according to claim 4 wherein at least one of said pressure connector, said line connector, and said closable side access are structured as a Luer lock.

6. The gas flow reversing apparatus according to claim 1 wherein at least one of said main piece, said branching piece and said fluid connection to said pressured gas supply is structured so as to be closable to prevent the flow of gas therethrough.

7. The gas flow reversing apparatus according to claim 1 wherein the ergonomically shaped housing is adapted to the human hand.

8. The gas flow reversing apparatus according to claim 1 wherein said at least one outlet opening is structured to switch between the first closed state and the second opened state.

9. The gas flow reversing apparatus according to claim 1 wherein said main piece and said branching piece together form approximately a T-shaped configuration with said main piece as crossbeam.

10. The gas flow reversing apparatus according to claim 1 wherein said main piece and said branching piece together form approximately a Y-shaped configuration with said at least one outlet opening forming the bottom of the Y.

11. The gas flow reversing apparatus according to claim 1 wherein said main piece and said branching piece are made substantially of plastic, and said nozzle comprises plastic or a metal insert, and said main piece including said pressure connector are encapsulated in said housing.

12. A gas flow reversing apparatus, the gas flow reversing apparatus comprising:
   a ventilating pressurized gas supply, the ventilating pressurized gas supply supplying oxygen; and
   a gas flow reversing element comprising:
      a main piece having first and second ends, said first end of said main piece defining at least one closable outlet opening, said at least one outlet opening being adjustable between a first closed state and a second open state, and wherein said main piece defines a mixing channel;
      a branching piece extending from said main piece to a distal end;
      a line connector connected to said distal end of said branching piece;
      a pressure connector connected to said second end of said main piece, said pressure connector being fluidly connected to the ventilating pressurized gas supply; and
      a nozzle being configured and arranged in said main piece in such a way that, when said at least one outlet opening is disposed in said second open state, a gas flow generated by the ventilating pressurized gas supply (i) flows to said pressure connector and through said nozzle and through said mixing channel to said at least one outlet opening and (ii) generates a gas flow in said branching piece in a direction toward said at least one outlet opening, wherein the gas flow through said main piece from said branching piece to said at least one outlet opening has a flow cross section that is substantially constant or that increases in the direction of said at least one outlet opening with a volumetric flow rate which, at an excess pressure of 0.5 to 5 bar above atmospheric pressure at said pressure connector, is at least 8 liters per minute, said nozzle also being configured and arranged in said main piece in such a way that, when said at least one outlet opening is disposed in said first closed state, a gas flow generated by the ventilating pressurized gas supply flows to said pressure connector and through said distal end of said branching piece towards said line connector; and
   wherein the gas flow reversing element is arranged in an ergonomically shaped housing and the at least one closable outlet opening of the main piece is configured to be closed by closing an opening in the ergonomically shaped housing.

13. The gas flow reversing apparatus according to claim 12 wherein the volumetric flow rate in said branching piece is at least 0.4 times the volumetric flow rate through said pressure connector at an excess pressure of 0.5 to 5 bar at said pressure connector.

14. The gas flow reversing apparatus according to claim 12 wherein the volumetric flow rate in said branching piece is approximately 0.4 to 2 times the volumetric flow rate through said pressure connector at an excess pressure of 0.5 to 5 bar at said pressure connector.

15. The gas flow reversing apparatus according to claim 12 wherein the length of said mixing channel and the internal diameter of said nozzle have a ratio of between 2:1 and 200:1.

16. The gas flow reversing apparatus according to claim 15 wherein the length of said mixing channel and the internal diameter of said nozzle have a ratio of between 5:1 and 100:1.

17. The gas flow reversing apparatus according to claim 16 wherein the internal diameter of said mixing channel and the internal diameter of said nozzle have a ratio of between 2:1 and 6:1.

18. The gas flow reversing apparatus according to claim 17 wherein the ratio of the internal diameter of said mixing channel and said internal diameter of said branching piece is between 1:2 and 2:1.

19. The gas flow reversing apparatus according to claim 12 wherein at least one of said main piece and said branching piece defines at least one safety opening.

20. The gas flow reversing apparatus according to claim 19 wherein said at least one outlet opening and said at least one safety opening are structured such that they can selectively be closed either individually or together and either completely or partially.

21. The gas flow reversing apparatus according to claim 19 wherein said branching piece and the line connected to said line connector defines a closable side access.

22. The gas flow reversing apparatus according to claim 21 wherein at least one of said pressure connector, said line connector, and said closable side access are structured as a Luer lock.

23. The gas flow reversing apparatus according to claim 12 wherein the ergonomically shaped housing is adapted to the human hand.

24. The gas flow reversing apparatus according to claim 12 wherein said at least one outlet opening is structured to be rotated between the first closed state and the second opened state.

25. The gas flow reversing apparatus according to claim 12 wherein said main piece and said branching piece together form approximately a T-shaped configuration with said main piece as crossbeam.

26. The gas flow reversing apparatus according to claim 12 wherein said main piece and said branching piece together form approximately a Y-shaped configuration with said at least one outlet opening forming the bottom of the Y.

27. A method for operating a gas flow reversing apparatus, comprising:

providing a ventilating pressurized gas supply, the ventilating pressurized gas supply supplying oxygen;

providing a gas flow reversing apparatus, the gas flow reversing apparatus comprising:

a main piece having first and second ends, the first end of the main piece defining at least one closable outlet opening, the at least one outlet opening being adjustable between a first closed state and a second open state;

a branching piece extending from the main piece to a distal end;

a line connector connected to the distal end of the branching piece;

a pressure connector connected to the second end of the main piece, the pressure connector being structured to be fluidly connected to the ventilating pressurized gas supply; and a nozzle being configured and arranged in the main piece in such a way that, when the at least one outlet opening is disposed in the second open state, a gas flow generated by the ventilating pressurized gas supply (i) flows to the pressure connector and through the nozzle to the at least one outlet opening and (ii) generates a gas flow in the branching piece in a direction toward the at least one outlet opening, wherein the gas flow through the main piece from the branching piece to the at least one outlet opening has a flow cross section that is substantially constant or that increases in the direction of the at least one outlet opening, the nozzle also being configured and arranged in the main piece in such a way that, when the at least one outlet opening is disposed in the first closed state, a gas flow generated by the ventilating pressurized gas supply flows to the pressure connector and through the distal end of the branching piece towards the line connector; and wherein the gas flow reversing element is arranged in an ergonomically shaped housing and the at least one closable outlet opening of the main piece is configured to be closed by closing an opening in the ergonomically shaped housing;

providing a catheter or a cannula;

connecting the catheter or the cannula to the line connector with or without a tube in between;

inserting the catheter or cannula into the airway of a patient;

fluidly connecting the pressure connector of the gas flow reversing apparatus to the ventilating pressurized gas supply; and supplying gas from the ventilating pressurized gas supply to the pressure connector of the gas flow reversing apparatus wherein a substantially constant gas pressure is applied to the pressure connector, and, in order to generate a gas flow to the line connector, the at least one outlet opening is closed and, in order to generate a gas flow from the line connector in the direction of the at least one outlet opening, the at least one outlet opening is opened.

28. The method according to claim 27 wherein the branching piece of the gas flow reversing apparatus defines a closable side access and further comprising:

providing a measuring device for measuring carbon dioxide content; and attaching the measuring device to the closable side access so that the measuring device can measure the carbon dioxide content of the gas or gas mixture flowing past the closable side access.

29. A method for ventilating a patient, or assisting the breathing of a patient, comprising:

providing a ventilating pressurized gas supply, the ventilating pressurized gas supply supplying oxygen;

providing a gas flow reversing apparatus, the gas flow reversing apparatus comprising:

a main piece having first and second ends, the first end of the main piece defining at least one closable outlet opening, the at least one outlet opening being adjustable between a first closed state and a second open state;

a branching piece extending from the main piece to a distal end;

a line connector connected to the distal end of the branching piece;

a pressure connector connected to the second end of the main piece, the pressure connector being structured to be fluidly connected to the ventilating pressurized gas supply; and a nozzle being configured and arranged in the main piece in such a way that, when the at least one outlet opening is disposed in the second open state, a gas flow generated by the ventilating pressurized gas supply (i) flows to the pressure connector and through the nozzle to the at least one outlet opening and (ii) generates a gas flow in the branching piece in a direction toward the at least one outlet opening, wherein the gas flow through the main piece from the branching piece to the at least one outlet opening has a flow cross section that is substantially constant or that increases in the direction of the at least one outlet opening, the nozzle also being configured and arranged in the main piece in such a way that, when the at least one outlet opening is disposed in the first closed state, a gas flow generated by the ventilating pressurized gas supply flows to the pressure connector and through the distal end of the branching piece towards the line connector; and wherein the gas flow reversing element is arranged in an ergonomically shaped housing and the at least one closable outlet opening of the main piece is configured to be closed by closing an opening in the ergonomically shaped housing;

providing a catheter or a cannula;

connecting the catheter or the cannula to the line connector with or without a tube in between;

inserting the catheter or cannula into the airway of a patient;

fluidly connecting the pressure connector of the gas flow reversing apparatus to the ventilating pressurized gas supply; and supplying oxygen from the ventilating pressurized gas supply to the pressure connector of the gas flow reversing apparatus wherein an excess pressure of between 0.5 and 5 bar is set up at the pressure connector and the at least one outlet opening is closed intermittently such that oxygen passes into the patient's airway and the at least one outlet opening is opened at intervals in order to aspirate gas out from the patient's airway.

30. The method according to claim 29 wherein the branching piece of the gas flow reversing apparatus defines a closable side access and further comprising:

providing a measuring device for measuring carbon dioxide content;

attaching the measuring device to the closable side access so that the measuring device can measure the carbon dioxide content of the gas or gas mixture flowing past the closable side access; and opening the at least one outlet opening at intervals and for at least long enough to generally maintain a characteristic measured value of carbon dioxide content for the gas or gas mixture aspirated from the airway.

31. A method of ameliorating breathing obstructions in a subject, comprising:
providing a ventilating pressurized gas supply, the ventilating pressurized gas supply supplying oxygen;
providing a gas flow reversing apparatus, the gas flow reversing apparatus comprising:
a main piece having first and second ends, the first end of the main piece defining at least one closable outlet opening, the at least one outlet opening being adjustable between a first closed state and a second open state;
a branching piece extending from the main piece to a distal end;
a line connector connected to the distal end of the branching piece;
a pressure connector connected to the second end of the main piece, the pressure connector being structured to be fluidly connected to the ventilating pressurized gas supply; and
a nozzle being configured and arranged in the main piece in such a way that, when the at least one outlet opening is disposed in the second open state, a gas flow generated by the ventilating pressurized gas supply (i) flows to the pressure connector and through the nozzle to the at least one outlet opening and (ii) generates a gas flow in the branching piece in a direction toward the at least one outlet opening, wherein the gas flow through the main piece from the branching piece to the at least one outlet opening has a flow cross section that is substantially constant or that increases in the direction of the at least one outlet opening, the nozzle also being configured and arranged in the main piece in such a way that, when the at least one outlet opening is disposed in the first closed state, a gas flow generated by the ventilating pressurized gas supply flows to the pressure connector and through the distal end of the branching piece towards the line connector; and
wherein the gas flow reversing element is arranged in an ergonomically shaped housing and the at least one closable outlet opening of the main piece is configured to be closed by closing an opening in the ergonomically shaped housing;
providing a catheter or a cannula;
connecting the catheter or the cannula to the line connector with or without a tube in between;
inserting the catheter or cannula into the airway of a subject;
fluidly connecting the pressure connector of the gas flow reversing apparatus to the ventilating pressurized gas supply;
supplying oxygen from the ventilating pressurized gas supply to the pressure connector of the gas flow reversing apparatus; and
opening and closing the at least one outlet opening intermittently to inspirate and aspirate the subject such that the subject is normoventilated.

32. The method according to claim 31 wherein the catheter has a maximum diameter of 3.5 mm.

33. The method according to claim 31 wherein the flow rate of the inspirated and aspirated gas is approximately 12 to 20 liters per minute.

34. The method according to claim 31 wherein the flow rate of the inspirated and aspirated gas is approximately 15 liters per minute.

* * * * *